(12) United States Patent
Dao

(10) Patent No.: US 11,857,702 B2
(45) Date of Patent: Jan. 2, 2024

(54) LUBRICATION METHOD

(71) Applicant: NATVI, Corbeil-Essonnes (FR)

(72) Inventor: Vi Thuy Dao, Fresnes (FR)

(73) Assignee: NATVI, Corbeil-Essonnes (FR)

( * ) Notice: Subject to any disclaimer, the term of this patent is extended or adjusted under 35 U.S.C. 154(b) by 555 days.

(21) Appl. No.: 17/269,590

(22) PCT Filed: Aug. 21, 2019

(86) PCT No.: PCT/EP2019/072402
§ 371 (c)(1),
(2) Date: Feb. 19, 2021

(87) PCT Pub. No.: WO2020/039008
PCT Pub. Date: Feb. 27, 2020

(65) Prior Publication Data
US 2021/0316047 A1    Oct. 14, 2021

(30) Foreign Application Priority Data

Aug. 22, 2018  (FR) ...................................... 1857583

(51) Int. Cl.
*A61L 31/10*    (2006.01)
*C08L 5/08*    (2006.01)
*A61L 31/14*    (2006.01)

(52) U.S. Cl.
CPC ............... *A61L 31/10* (2013.01); *A61L 31/14* (2013.01); *C08L 5/08* (2013.01); *A61L 2400/10* (2013.01); *A61L 2420/02* (2013.01)

(58) Field of Classification Search
None
See application file for complete search history.

(56) References Cited

U.S. PATENT DOCUMENTS

| | | |
|---|---|---|
| 4,716,224 A | 12/1987 | Sakurai et al. |
| 6,221,425 B1 | 4/2001 | Michal et al. |
| 2006/0002967 A1 | 1/2006 | Smestad et al. |
| 2009/0197829 A1 | 8/2009 | Mabille et al. |
| 2009/0253599 A1 | 10/2009 | Luczak et al. |
| 2015/0376457 A1 | 12/2015 | Michelot |

FOREIGN PATENT DOCUMENTS

| | | |
|---|---|---|
| CN | 101563116 A | 10/2009 |
| CN | 101678397 A | 3/2010 |
| CN | 101932610 A | 12/2010 |
| CN | 101990440 A | 3/2011 |
| CN | 102105501 A | 6/2011 |
| CN | 105121034 A | 12/2015 |
| CN | 106334219 A | 1/2017 |
| CN | 106729997 A | 5/2017 |
| EP | 0161887 A2 | 11/1985 |
| FR | 3001642 A1 | 8/2014 |

OTHER PUBLICATIONS

Frison, Céline; International Search Report; PCT/EP2019/072402; dated Nov. 4, 2019; 4 pages.
Khunmanee, Sureerat, et al.; "Crosslinking method of hyaluronic-based hydrogel for biomedical applications"; Journal of Tissue Engineering, vol. 8; dated Sep. 6, 2017; XP002791499; pp. 1-16.

*Primary Examiner* — Danah Al-Awadi
(74) *Attorney, Agent, or Firm* — Bradley Arant Boult Cummings LLP

(57) ABSTRACT

The invention relates to a method for lubricating a component consisting of a hydrophilic compound crosslinked by means of a water-soluble transition metal chelate.

10 Claims, 2 Drawing Sheets

LUBRICATION METHOD

The invention relates to a lubrication method.

The functionalization of the surface of materials used for various applications, in particular in the medical field, is a determining factor for the interaction of materials with the environment. However, such a modification is not always straightforward.

Medical devices can be covered with a multitude of compositions or compounds depending on the intended uses. It may in particular be necessary to cover a medical device with a composition comprising a pharmaceutical agent or an agent allowing hydration, in particular in the context of implantation in an organism. Likewise, the use of a medical device can be improved by covering it with a lubricating composition.

However, it is often necessary for these types of compositions to be both biocompatible and to have good hold on the surface on which these compositions are deposited.

Patent application FR 3001642 is already known from the prior art, which describes a method for covering a hydrophobic surface with a hydrophilic compound. The method described in this document involves superposing a first layer of an amphiphilic compound exhibiting self-assembly properties and a second layer of a hydrophilic polymer, in particular polysaccharides.

Such a method has been found to be very useful in rendering a hydrophobic surface hydrophilic. However, this method does not make it possible to provide surfaces which would be both biocompatible and useful for the sufficiently durable lubrication of the surfaces, in particular to promote the repetitive sliding of another surface on this covered surface.

In addition, there is a need to improve the method from the prior art, in particular due to the relative fragility of the resulting covering and its lack of resistance to friction, despite its high biocompatibility.

One of the means for stabilizing the structures involves the crosslinking of the layer of hydrophilic polymers.

However, the commonly used crosslinking agents are either unstable in aqueous solutions or lead to the formation of crosslinked polymers with very low lubricating ability.

The invention therefore aims to overcome these drawbacks.

One of the objects of the invention is to provide a sufficiently durable method for lubricating a structure, in particular consisting of crosslinked polymers.

Another object of the invention is to provide a lubricated element obtained by said method.

Yet another object of the invention is to provide a method for lubricating a surface which is structurally not lubricated in a simple and rapid manner, as well as the resulting surface.

In addition, the invention relates to a method for lubricating an element essentially consisting of a crosslinked hydrophilic polymer, said method comprising:
1. a step of bringing said element essentially consisting of a crosslinked hydrophilic polymer into contact with a solution of a free or non-crosslinked hydrophilic polymer, said element essentially consisting of a crosslinked hydrophilic polymer having been crosslinked by means of a crosslinking agent which is a transition-metal chelate that is soluble and stable in water.

The invention is based on the surprising finding made by the inventors that the crosslinking of hydrophilic polymers by a transition-metal chelate that is soluble and stable in water not only makes it possible to obtain a polymer structure of said stiffened hydrophilic polymer, in particular in the form of gel, but also that the crosslinking of the polymer structure by a water-soluble transition-metal chelate makes it possible to maintain a layer of non-crosslinked hydrophilic polymers which thus provides said stiffened hydrophilic polymer structure with lubricating properties.

Crosslinking agents can include any compound of a transition metal such as titanium, zirconium, chromium, or hafnium. The most suitable crosslinking agents are complex ions derived from tetramethyl orthotitanate, tetraethyl titanates, tetrapropyl titanates, tetrapropyl zirconates, and tetrabutyl zirconates, which are made soluble in water by reaction with ligands such as beta-diketone compounds, amino alcohols, hydroxylamines, ethoxylated alcohols, lactones, and polyacrylic acids. More specific examples are cited for reactions with ligands such as triethanolamine, acetylacetonate, lactic acid, etc.

The hydrophilic polymer according to the invention can be, without this being limiting, formed by anionic or cationic polymers, acidic polymers, polymers of amines or amino acids, and biologically and/or pharmaceutically acceptable salts thereof. It is also possible to have mixtures of the above-mentioned polymers. The following can be cited as examples of polymers that can be used in the invention: collagen, collagen modified by oxidation, polysaccharides, alginates, hyaluronic acid, polylysine, etc. Such examples are indicative and should not be considered as limiting the scope of the invention.

It is advantageous in the invention to select the hydrophilic polymer from polycations, for example polyamines, histones (proteins surrounding the DNA of eukaryotic cells rich in basic amino acids), chitosan, polylysine, etc.

Mucopolysaccharides or glycoproteins are also hydrophilic polymers that are covered by the present invention.

Advantageously, the invention relates to a method for lubricating an element essentially consisting of a crosslinked hydrophilic polymer, said method comprising:
1. a step of bringing said element essentially consisting of a crosslinked hydrophilic polymer into contact with a solution of free or non-crosslinked hyaluronic acid, said element essentially consisting of a crosslinked hydrophilic polymer having been crosslinked by means of a crosslinking agent which is a transition-metal chelate that is soluble and stable in water.

Advantageously, the invention relates to a method for lubricating an element essentially consisting of crosslinked hyaluronic acid, said method comprising:
1. a step of bringing said element essentially consisting of crosslinked hyaluronic acid into contact with a solution of a free or non-crosslinked hydrophilic polymer, said element essentially consisting of crosslinked hyaluronic acid having been crosslinked by means of a crosslinking agent which is a transition-metal chelate that is soluble and stable in water.

Advantageously, the invention relates to a method for lubricating an element essentially consisting of crosslinked hyaluronic acid, said method comprising:
1. a step of bringing said element essentially consisting of crosslinked hyaluronic acid into contact with a solution of free or non-crosslinked hyaluronic acid, said element essentially consisting of crosslinked hyaluronic acid having been crosslinked by means of a crosslinking agent which is a titanium chelate that is soluble and stable in water.

In one of its aspects, the invention is based on the surprising finding made by the inventors that the crosslinking of hyaluronic acid by a titanium chelate that is soluble and stable in water not only makes it possible to obtain a polymer structure of said stiffened hyaluronic acid, in particular in the form of gel, but also that the crosslinking of the polymer structure by a water-soluble titanium chelate makes it possible to maintain a layer of non-crosslinked hyaluronic acid which thus provides said stiffened hyaluronic acid structure with lubricating properties.

More particularly, the inventors surprisingly found that the water-soluble Ti chelates were good hyaluronic-acid crosslinking agents and good agents for allowing the retention of free hyaluronic acid on a structure crosslinked with said water-soluble Ti chelates.

It should be noted that Ti chelates which are insoluble in water or which degrade once dissolved in water (i.e. which are not stable in watery do not make it possible to implement the invention, and are therefore in fact excluded from the present invention.

One of the problems with crosslinking agents is their solubility in water. This is because many crosslinking agents are known to be soluble in organic solvents but to be very unstable in water. However, it is essential that the crosslinking agent used in the invention is soluble and active in water, otherwise it is not possible to use them to crosslink the hyaluronic acid, which is water-soluble.

According to the above-mentioned method, an element essentially consisting of hyaluronic acid crosslinked by said crosslinking agent, which has preferably been rinsed with water beforehand, is simply used, and a solution of hyaluronic acid is deposited thereon. Crosslinking with titanium chelate allows non-crosslinked hyaluronic acid to be retained on the surface of the crosslinked structure.

This very simple and environmentally friendly process results in a structure being obtained that is composed of two layers: a layer of crosslinked hyaluronic acid covered by a layer of non-crosslinked hyaluronic acid.

It is particularly advantageous for the hyaluronic acid added in step a) to be hyaluronic acid at a concentration of 0.1 to 0.5% in water (mass/volume or m/v), in particular of 0.2 to 0.3% (m/v) in water.

In an advantageous embodiment, said water-soluble crosslinking agent is a chelate of the following formula 1:

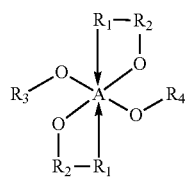

(1)

where A is Ti, Zr or Hf and where $R_1$ is a functional group containing an oxygen or nitrogen atom, $R_2$ represents two or three carbon atoms, and $R_3$ and $R_4$ represent a linear or branched or cyclic $C_3$-$C_4$ alkyl, comprising a methyl group, an ethyl group, a propyl or methylethyl or cyclopentyl group, a butyl or isopropyl or sec-butyl or Cert-butyl or cyclobutyl group.

The particularly advantageous compounds or crosslinking agents according to the invention therefore correspond to the following formula 1a:

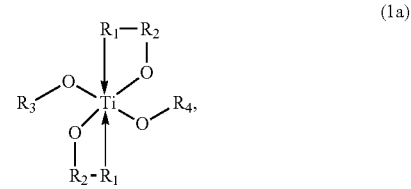

(1a)

where $R_1$ is a functional group containing an oxygen or nitrogen atom, $R_2$ represents two or three carbon atoms, and $R_3$ and $R_4$ represent a linear or branched or cyclic $C_1$-$C_4$ alkyl, comprising a methyl group, an ethyl group, a propyl or methylethyl or cyclopentyl group, a butyl or isopropyl or sec-butyl or tert-butyl or cyclobutyl group.

Yet more advantageously, said crosslinking agent is one of the following compounds:

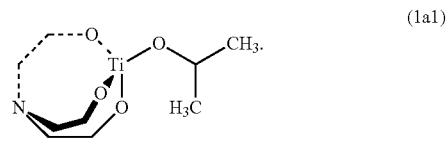

(1a1)

or titanium(IV) (triethanolaminato)isopropoxide (titanium-complex triethanolamine Tyzor TE) CAS no.: 74665-17-1,

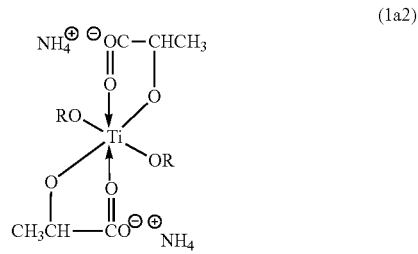

(1a2)

Dihydroxybis(ammonium lactato)titanium(IV) TYZOR® LA—lactic acid titanate chelate, ammonium salt CAS no. 65104-06-5, and In an advantageous embodiment, the invention relates to the above-mentioned method, wherein said crosslinking agent is the crosslinking agent of the following formula 1a1:

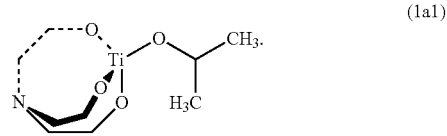

(1a1)

The compound of formula 1a1 is also known by the name Tyzor TE, in particular sold by DuPont, or titanium-complex triethanolamine (CAS no. 74665-17-1).

In another advantageous embodiment, the invention relates to the above-mentioned method, wherein said crosslinking agent is the crosslinking agent of the following formula 1 b:

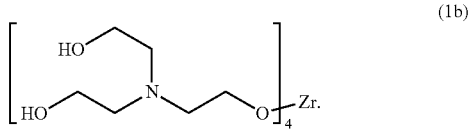

In yet another embodiment, the invention relates to the above-mentioned method, further comprising:
- b) a step of crosslinking the free or non-crosslinked hydrophilic polymer brought into contact with said composition essentially consisting of hydrophilic polymer crosslinked using an above-mentioned crosslinking agent, in particular of formula 1, in order to obtain a second layer of composition essentially consisting of crosslinked hydrophilic polymer, and
- c) a step of bringing the second layer of composition essentially consisting of crosslinked hydrophilic polymer into contact with a solution of free hydrophilic polymer.

Advantageously, the invention relates to the above-mentioned method, further comprising:
- b) a step of crosslinking the free or non-crosslinked hyaluronic acid brought into contact with said composition essentially consisting of hydrophilic polymer crosslinked using an above-mentioned crosslinking agent, in particular of formula 1a, in order to obtain a second layer of composition essentially consisting of crosslinked hyaluronic acid, and
- c) a step of bringing the second layer of composition essentially consisting of crosslinked hyaluronic acid into contact with a solution
  - either of free hyaluronic acid
  - or of free hydrophilic polymer.

More advantageously, the invention relates to the above-mentioned method, further comprising:
- b) a step of crosslinking the free or non-crosslinked hydrophilic polymer brought into contact with said composition essentially consisting of hyaluronic acid crosslinked using an above-mentioned crosslinking agent, in particular of formula 1a, in order to obtain a second layer of composition essentially consisting of crosslinked hydrophilic polymer, and
- c) a step of bringing the second layer of composition essentially consisting of crosslinked hydrophilic polymer into contact with a solution
  - either of free hyaluronic acid
  - or of free hydrophilic polymer.

In the above, said hydrophilic polymer is advantageously a lubricating hydrophilic biopolymer such as lubricating mucopolysaccharide or glycoprotein.

In yet another advantageous embodiment, the invention relates to the above-mentioned method, further comprising:
- b) a step of crosslinking the free or non-crosslinked hyaluronic acid brought into contact with said composition essentially consisting of hyaluronic acid crosslinked using a crosslinking agent of formula 1a in order to obtain a second layer of composition essentially consisting of crosslinked hyaluronic acid, and
- c) a step of bringing the second layer of composition essentially consisting of crosslinked hyaluronic acid into contact with a solution of free hyaluronic acid.

In order to stabilize the structure obtained after step a) of the method according to the invention, it may be advantageous to crosslink, using the above-mentioned crosslinking compound, the layer of free hyaluronic acid which has been deposited on the element essentially consisting of crosslinked hyaluronic acid as defined above. In order to lubricate this second lubricating layer, a layer of free or non-crosslinked hyaluronic acid is then deposited on the last layer of crosslinked hyaluronic acid in step b).

The structure thus obtained consists of two layers of crosslinked hyaluronic acid which are directly in contact but separate, and a layer of non-crosslinked hyaluronic acid.

Advantageously, steps b) and c) are repeated at least once.

The purpose of repeating steps b) and c) is to stabilize the structures thus obtained, while preserving, with step c), a lubricated element due to the presence of the free hyaluronic acid layer.

When steps b) and c) are repeated, the structure will have 3 layers of crosslinked hyaluronic acid, the last layer being covered by a layer of free or non-crosslinked hyaluronic acid or a layer of a non-crosslinked lubricating hydrophilic biopolymer.

The invention also relates to a lubricated element essentially consisting of at least one layer of a hydrophilic polymer, in particular a hydrophilic polymer as mentioned above, which is crosslinked using a crosslinking agent as defined above, said at least one layer of a hydrophilic polymer being covered by a layer of non-crosslinked hydrophilic polymer, in particular a layer of a non-crosslinked lubricating hydrophilic biopolymer.

Advantageously, the invention also relates to a lubricated element essentially consisting of at least one layer of a hydrophilic polymer, in particular a hydrophilic polymer as mentioned above, which is crosslinked using a crosslinking agent as defined above, said at least one layer of a hydrophilic polymer being covered by a layer of non-crosslinked hyaluronic acid.

The invention also relates to a lubricated element essentially consisting of at least one layer of hyaluronic acid which is crosslinked using a crosslinking agent as defined above, said at least one layer of hyaluronic acid being covered by a layer of non-crosslinked hydrophilic polymer, in particular a layer of a non-crosslinked lubricating hydrophilic biopolymer.

This element is both relatively solid thanks to the crosslinking, and often in the form of a gel, and has good lubrication due to the presence of free or non-crosslinked hyaluronic acid, in particular a layer of a non-crosslinked lubricating hydrophilic biopolymer, on its outer upper layer.

Advantageously, the invention relates to a lubricated element essentially consisting of at least one layer of hyaluronic acid crosslinked by a crosslinking agent as defined above, said at least one layer of crosslinked hyaluronic acid being covered by a layer of non-crosslinked hyaluronic acid, said element being obtainable according to the method specified above.

In another aspect, the invention relates to a method for lubricating a hydrophobic surface or a hydrophobic support, comprising:
1. a step of bringing the hydrophobic surface into contact, with a view to covering it, with a first composition comprising a. a solvent, and
b. a solute comprising an amphiphilic compound capable of self-assembly and of interacting with said surface, the self-assembly of said compound and the interaction with the surface taking place by means of bonds other than covalent or ionic bonds,
said solvent being compatible with said compound and said hydrophobic surface,
1. a subsequent step of rinsing said hydrophobic surface covered in the previous step with an aqueous solution,
2. a step of bringing the rinsed surface into contact with a second hydrophilic composition comprising a hydrophilic polymer,
3. a step of crosslinking the hydrophilic polymer present on the surface obtained in the previous step using a crosslinking agent in order to obtain a first layer of crosslinked hydrophilic polymer, and
4. a step of bringing the first layer of crosslinked polymer into contact with a solution of free hydrophilic polymer, wherein said crosslinking agent is a transition-metal chelate, in particular titanium chelate or zirconium chelate or hafnium chelate that is soluble and stable in

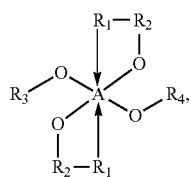

(1)

where A is Ti, where $R_1$ is a functional group containing an oxygen or nitrogen atom. $R_2$ represents two or three carbon atoms, and $R_3$ and $R_4$ represent a linear or branched or cyclic $C_1$-$C_4$ alkyl.

In the invention, the term "hydrophobic surface" means the surface or a surface of a medical device. The term "hydrophobic support" also means a face or a part of a medical device.

Therefore, in the invention, the "surface" or the "support" corresponds to a solid medical device, in particular that which is likely to cause friction while penetrating the human or animal body. For example, without being limiting, the support may be: the inside of a syringe, the plunger of a syringe, the rubber of the plunger of a syringe, a hollow needle, whether or not used with a syringe (whether it is acts on the outer surface of the needle or the channel thereat), a stent, a catheter (in particular for intracerebral, intracardiac, and vascular use as well as vascular guide wires), a lens (in particular a lens intended to be inserted into the eye), a probe, a drill, and more generally any medical or surgical instrument intended to allow the placement of an implant, a prosthesis suitable for being inserted into the human or animal body temporarily or permanently, a heart valve, a pacemaker, in particular an artificial pacemaker, an orthopedic implant, etc.

In the invention, the term "medical device" takes the legal meaning defined by French law, namely any instrument, device, equipment, material, product, or manufactured product, with the exception of products of human or animal origin, or any other article used alone or in combination, intended by the manufacturer for medical use in humans and the desired principal action of which is not obtained by pharmacological or immunological means or by metabolism, but the function of which may be assisted by such means.

The hydrophobic surfaces to be covered by the method of the invention are generally made of polymer materials of the thermoplastic type, such as polyethylene (PE), polypropylene (PP), polyethylene terephthalate (PET), polybutylene terephthalate (PBT), polyoxymethylene (POM), polyarylate (PAr), polyetherketone (PEK), fluorinated polymers (for example, polyvinylidene fluoride (PVDF), cyclic olefin polymers (COC) (for example polymers marketed under the brand name "TOPAS"), cyclic olefin copolymers (COP) (for example the copolymers marketed under the brand name "Zeonex"), polytetrafluoroethylene (PTFE), polychlorotrifluoroethylene (PCTFE)), polysulfone (PSU), ethylene-propylene-diene monomer (EPDM), or of the thermosetting type, such as synthetic rubbers (for example, halogenobutyl rubber, nitrile rubbers, polyisoprenes, and polychloroprenes) or of the thermoplastic elastomer type (for example, EPDM-PP copolymer marketed under the brand name "Santoprene," the styrene-ethylene-butylene-styrene (SEBS) block copolymer, etc.).

Other surfaces, such as stainless steel, gold, titanium, platinum, aluminum, an alloy of nickel and titanium or nitinol, tantalum, or silicones, can be covered according to the method according to the invention. The above-mentioned list is not limiting, and a person skilled in the art will understand that these are hydrophobic surfaces which can be used in particular in the context of the above-mentioned devices for medical use.

Advantageously, the invention relates to a method for lubricating a hydrophobic surface of a medical device which is likely to cause friction while penetrating the human body, said method comprising:

1. a step of bringing the hydrophobic surface of said medical device into contact, with a view to covering it, with a first composition comprising
a. a solvent, and
b. a solute comprising an amphiphilic compound capable of self-assembly and of interacting with said surface, the self-assembly of said compound and the interaction with the surface of said medical device taking place by means of bonds other than covalent or ionic bonds,
said solvent being compatible with said compound and said hydrophobic surface of said medical device,
1. a subsequent step of rinsing said hydrophobic surface of said medical device covered in the previous step with an aqueous solution,
2. a step of bringing the rinsed surface into contact with a second hydrophilic composition comprising a hydrophilic polymer,
3. a step of crosslinking the hydrophilic polymer present on the surface obtained in the previous step using a crosslinking agent in order to obtain a first layer of crosslinked hydrophilic polymer, and
4. a step of bringing the first layer of crosslinked polymer into contact with a solution of free hydrophilic polymer, wherein said crosslinking agent is a transition-metal chelate, in particular titanium chelate or zirconium chelate or hafnium chelate that is soluble and stable in water, in particular a chelate of the following formula 1:

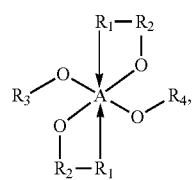

where A is Ti, where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

In the context of this aspect of the invention, the inventors have made the surprising observation that the crosslinking of the hydrophilic polymer stabilizes the structure with the self-assembling amphiphilic compound such that the hydrophilic polymer layer is not removed by simple friction. In addition, the inventors envisaged adding an additional layer of hydrophilic compound in order to lubricate the surface.

This observation was only possible with the use of soluble and active crosslinking agents in an aqueous solution. Indeed, since the first step of covering the support is depositing the amphiphilic composition on the support, said composition would be dissolved in an organic solvent which would serve to dissolve the crosslinking agent. In addition, a crosslinking agent for the hydrophilic composition which would be soluble only in an organic solvent would therefore strip the layer of amphiphilic compound, thus taking with it the hydrophilic polymer, and therefore it would no longer be capable of rendering the hydrophobic support hydrophilic.

The compound used in the context of step a) of the invention is an amphiphilic compound, i.e. a compound which has both at least one hydrophilic group and at least one hydrophobic group.

Self-assembly is the phenomenon by means of which compounds themselves form structures with a high degree of organization without external intervention. Schematically, these compounds can be considered to have an affinity that is sufficient for them to self-assemble.

A distinction is made between two types of self-assembly, namely intramolecular and intermolecular. Intramolecular self-assembly often produces complex polymers which have the potential to adopt a stable and well-defined structure. Intermolecular self-assembly defines the ability of certain molecules to form supramolecular assemblies. An example of this type of self-assembly relates to the formation of micelles from surfactants in solution. Self-assembly is generally due to bonds of the van der Waals type. The stability of self-assembly results in large part from thermodynamic factors which favor ordered forms of matter (negentropy) over disordered states.

Self-assembly can occur spontaneously, for example in cells (where the membrane is made of a self-assembled lipid double layer) and other biological systems, as well as in artificial systems. This generally results in an increase in the internal organization of the system. Self-assembled biological systems, including self-assembled synthetic peptides and other biomaterials, exhibit greater ease of handling, biocompatibility, and functionality. These advantages are directly due to self-assembly from biocompatible precursors that create nanoscale synthesized biomaterials.

In the first step a) of the method, only the intermolecular interactions come into play. The forces caused by the self-assembly of these compounds are sufficient to allow the compound to interact with the substrate, and to remain deposited uniformly thereon, without it being necessary to involve physicochemical interactions therewith.

In other words, there is no covalent bond between the self-assembling compound and the surface covered thereby. Likewise, there are no ionic bonds between the self-assembling compound and the surface covered thereby.

In the first step of the method according to the invention, a solvent solution comprising a self-assembling compound is brought into contact with the surface to be covered; "said solvent is compatible with said compound and said hydrophobic surface", which means that the self-assembling compound is soluble in said solvent, and that the solvent does not exert an effect that drastically alters the nature and the surface of the substrate to be covered.

In an advantageous embodiment, the solvent used is capable of causing slight abrasion of the surface to be covered, such that micro-depressions can be caused on the surface of said surface.

Advantageously, the surface is cleaned and degreased beforehand in order to remove traces of compounds which may impair the self-assembly of the compounds.

Depending on the nature of the surface, it can be cleaned and degreased with an appropriate solvent. A person skilled in the art is able to determine the solvent or mixtures of solvents required. The example part below gives some guidance.

In the invention, the term "solvent compatible with said compound" is understood to mean a solvent capable of dissolving said self-assembling amphiphilic compound. A person skilled in the art can easily determine the solvent or the solvent mixtures that are most suitable for dissolving the amphiphilic compound. The term "solvent compatible with said hydrophobic surface" means a solvent that is capable of not degrading or altering the hydrophobic surface.

In another embodiment of the invention, the first step of the method can be implemented directly during the manufacture of the hydrophobic surface to be covered. For example, the self-assembling compound, considered to be an additive in the form of powder or granules, optionally in the form of a solution, in particular of a highly concentrated solution, is added to granules of hydrophobic polymers, and the mixture thus obtained is then subjected to fusion followed by extrusion. In this embodiment, during the cooling, the self-assembling compounds slowly migrate to the superficial portions of the surface that is forming, and the polar portions of the compound are exposed to the exterior of the surface.

In yet another advantageous embodiment, the surface to be covered is treated with a solvent of the polymer for a specific length of time, such that microabrasion appears on the superficial parts of the surface. Such abrasions allow the self-assembling compound to diffuse and regroup and allow its hydrophilic portion to be exposed to the exterior of the substrate.

In the second step b) of the method, the layer of amphiphilic compound is washed with an aqueous solution. Once washed, the surface can advantageously be dried.

In the third step c) of the method according to the invention, the hydrophobic surface, covered with the self-assembling amphiphilic compound which has been washed and optionally dried, is covered, or coated, with a second composition comprising at least one or more hydrophilic polymers.

The second composition comprising at least one or more hydrophilic polymers is conventionally dissolved and brought into contact with the surface that has been washed beforehand and optionally dried in the preceding step.

It is advantageous in the invention to select the hydrophilic polymer such that it has an affinity for the amphiphilic self-assembling compound.

In addition, it would be advantageous to use polycations, for example polyamines, histones (proteins surrounding the DNA of eukaryotic cells rich in basic amino acids), chitosan, polylysine, etc., when the self-assembling compound comprises an anionic polar portion and to select polyanions, such as glycosaminoglycans, such as chondroitin sulfate, heparin or heparan sulfates, keratin sulfates, dermatan sulfate, and hyaluronic acid, polypeptides, in particular synthetic peptides such as polyglutamic acid, polyaspartic acid, etc., when the self-assembling compound comprises a cationic polar portion.

Advantageously, the hydrophilic polymer interacts with the self-assembling amphiphilic compound by means of ionic bonds.

In an advantageous embodiment, the invention relates to a method for lubricating a hydrophobic support, comprising:
  a) a step of covering the support with a first composition comprising a solvent, and
    a solute selected from stearylamine or stearic acid, to obtain a support covered with said first composition, said solvent being compatible with said solute and said hydrophobic surface,
  b) a subsequent step of rinsing said hydrophobic support covered with said first composition with an aqueous solution in order to obtain a hydrophobic support covered with said first rinsed composition, and
  c) a step of bringing said hydrophobic support covered with said first rinsed composition into contact with free hyaluronic acid in order to obtain a surface having free hyaluronic acid,
  d) a step of crosslinking the free hyaluronic acid present on the surface obtained in the previous step using a crosslinking agent in order to obtain a first layer of crosslinked hyaluronic acid, and
  e) a step of bringing the first layer of crosslinked hyaluronic acid into contact with a solution of free hyaluronic acid;
wherein said crosslinking agent is a water-soluble titanium chelate, in particular a chelate of the following formula 1:

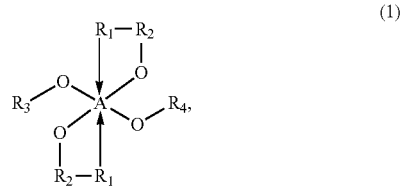

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

Yet more advantageously, the invention relates to a method for lubricating a hydrophobic support, comprising:
  a) a step of covering the support with a first composition comprising
    a solvent, and
    a solute essentially consisting of stearylamine, to obtain a support covered with said first composition, said solvent being compatible with said solute and said hydrophobic surface,
  b) a subsequent step of rinsing said hydrophobic support covered with said first composition with an aqueous solution in order to obtain a hydrophobic support covered with said first rinsed composition, and
  c) a step of bringing said hydrophobic support covered with said first rinsed composition into contact with free hyaluronic acid in order to obtain a surface having free hyaluronic acid,
  d) a step of crosslinking the free hyaluronic acid present on the surface obtained in the previous step using a crosslinking agent in order to obtain a first layer of crosslinked hyaluronic acid, and
  e) a step of bringing the first layer of crosslinked hyaluronic acid into contact with a solution of free hyaluronic acid; wherein said crosslinking agent is a water-soluble titanium chelate or zirconium chelate, in particular a chelate of the following formula 1:

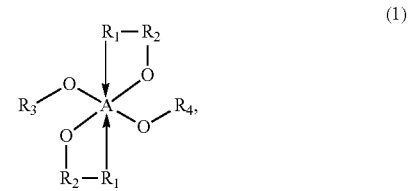

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

It may be advantageous for the above-mentioned step d) to be followed by a step of washing with an aqueous solution. This washing step makes it possible to remove the excess crosslinking agent and hydrolyzes the parts of the crosslinking agent which have not yet reacted with the hyaluronic acid.

In another embodiment, the crosslinking step d) is carried out at a temperature varying from 40 to 70° C., at atmospheric pressure, in particular from 45 to 65° C., in particular at 60° C. This heating step increases the reactivity of the crosslinking agent.

In another aspect, the invention relates to a method for lubricating a hydrophobic support, comprising:
  a) a step of covering the support with a first composition comprising
    a solvent, and
    a solute essentially consisting of stearic acid, to obtain a support covered with said first composition, said solvent being compatible with said solute and said hydrophobic surface,
  b) a subsequent step of rinsing said hydrophobic support covered with said first composition with an aqueous solution in order to obtain a hydrophobic support covered with said first rinsed composition, and
  c) a step of bringing said hydrophobic support covered with said first rinsed composition into contact with free chitosan in order to obtain a surface having free chitosan, said free chitosan being in solution at pH 5.5, d) a step of bringing said surface having free chitosan into contact with a solution of free hyaluronic acid to obtain a surface covered with hyaluronic acid, e) a step of crosslinking the free hyaluronic acid present on the surface obtained in the previous step using a crosslinking agent in order to obtain a first layer of crosslinked hyaluronic acid, and f) a step of bringing the first layer of crosslinked hyaluronic acid into contact with a solution of free hyaluronic acid; wherein said crosslinking agent is a water-soluble titanium chelate or zirconium chelate, in particular a chelate of the following formula 1:

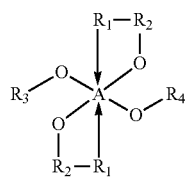
(1)

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

In the above-mentioned method in which the layer of stearic acid is covered with free chitosan, it may be advantageous after step c) to crosslink said free chitosan with a crosslinking agent of the above-mentioned formula 1.

The hydrophobic surfaces to be covered and lubricated by the method of the invention are generally made of polymer materials of the thermoplastic type, such as polyethylene (PE), polypropylene (PP), polyethylene terephthalate (PET), polybutylene terephthalate (PBT), polyoxymethylene (POM), polyarylate (PAr), polyetherketone (PETS), fluorinated polymers (for example, polyvinylidene fluoride (PVDF), cyclic olefin polymers (COC) (for example polymers marketed under the brand name "TOPAS"), cyclic olefin copolymers (COP) (for example the copolymers marketed under the brand name "Zeonex"), polytetrafluoroethylene (PTFE), polychlorotrifluoroethylene (PCTFE)), polysulfone (PSU), ethylene-propylene-diene monomer (EPDM), or of the thermosetting type, such as synthetic rubbers (for example, halogenobutyl rubber, nitrile rubbers, polyisoprenes, and polychloroprenes) or of the thermoplastic elastomer type (for example, EPDM-PP copolymer marketed under the brand name "Santoprene," the styrene-ethylene-butylene-styrene (SEBS) block copolymer, etc.).

Other surfaces, such as stainless steel, gold, titanium, platinum, aluminum, an alloy of nickel and titanium or nitinol, tantalum, or silicones, can be covered and lubricated according to the method according to the invention. The above-mentioned list is not limiting, and a person skilled in the art will understand that these are hydrophobic surfaces which can be used in particular in the context of devices for medical use.

Advantageously, the invention relates to the above-mentioned method for lubricating a hydrophobic support, wherein said crosslinking agent is the crosslinking agent of the following formula 1a1:

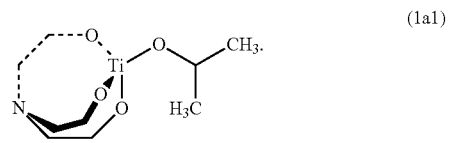
(1a1)

or of the following formula 1a2:

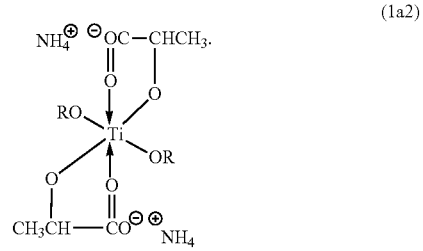
(1a2)

Advantageously, the invention relates to the above-mentioned method for lubricating a hydrophobic surface, wherein steps d) and e) are repeated at least once.

Advantageously, when chitosan is used, it is steps e) and f) which are repeated at least once.

In another aspect, the invention relates to a lubricated hydrophobic support obtainable according to the method defined above.

Advantageously, the invention relates to a hydrophobic support covered with a first layer of stearylamine or stearic acid, said first layer of stearylamine or stearic acid being covered by a first layer of hyaluronic acid crosslinked by a water-soluble titanium chelate, in particular a chelate of the following formula 1:

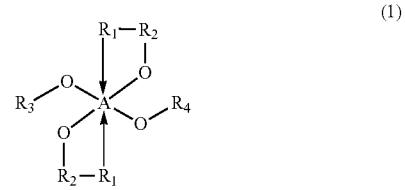
(1)

where A is Ti, and
where R1 is a functional group containing an oxygen or nitrogen atom, R2 represents two or three carbon atoms, and R3 and R4 represent a linear or branched or cyclic C1-C4 alkyl, said first layer of crosslinked hyaluronic acid being covered by a second layer of free hyaluronic acid.

In another embodiment, the invention relates to a hydrophobic support covered with a first layer of stearylamine, said first layer of stearylamine being covered by a first layer of hyaluronic acid crosslinked by a titanium chelate, in particular a chelate of the following formula 1:

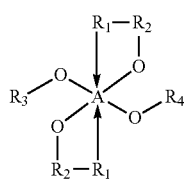
(1)

where A is Ti, Zr or Hf and, in particular of the following formula 1a:

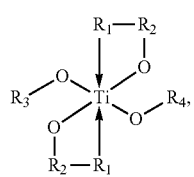
(1a)

and
where R1 is a functional group containing an oxygen or nitrogen atom, R2 represents two or three carbon atoms, and R3 and R4 represent a linear or branched or cyclic C1-C4 alkyl, said first layer of crosslinked hyaluronic acid being covered by a second layer of free hyaluronic acid.

More advantageously, the invention relates to a hydrophobic support covered with a first layer of stearic acid, said first layer of stearic acid being covered by a first layer of chitosan, said first layer of chitosan being covered by a first layer of hyaluronic acid crosslinked by a water-soluble titanium chelate or zirconium chelate, in particular a chelate of the following formula 1:

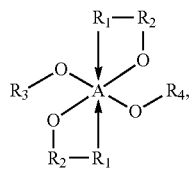
(1)

where A is Ti, in particular of the following formula 1a

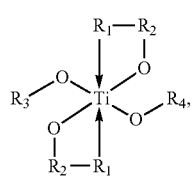
(1a)

where R1 is a functional group containing an oxygen or nitrogen atom, R2 represents two or three carbon atoms, and R3 and R4 represent a linear or branched or cyclic C1-C4 alkyl, said first layer of crosslinked hyaluronic acid being covered by a second layer of free hyaluronic acid.

Advantageously, said crosslinking agent is the compound of formula 1a1 mentioned above.

The invention also relates to a kit comprising:
1. a first composition essentially consisting of stearylamine or stearic acid,
2. a second composition comprising or essentially consisting of hyaluronic acid or chitosan, in particular having a concentration of from 0.1 to 0.5% ill/or in water, and
3. a crosslinking compound which is a water-soluble titanium chelate or zirconium chelate, in particular a chelate of the following formula 1:

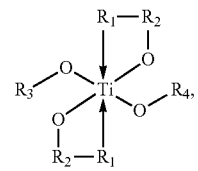

where A is Ti, in particular of the following formula 1a: and where $R_1$ is a functional group containing an oxygen or nitrogen atom, $R_2$ represents two or three carbon atoms, and $R_3$ and $R_4$ represent a linear or branched or cyclic $C_1$-$C_4$ alkyl, in particular the compound of the following formula 1a1:

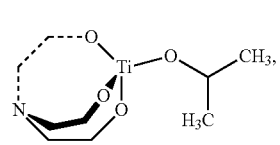
(1a1)

or of the following formula 1a2

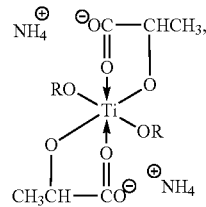
(1a2)

or a compound of the following formula 1b

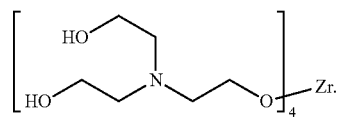
(1b)

The invention will be better understood in the light of the following examples and drawings.

BRIEF DESCRIPTION OF THE DRAWINGS

Brief Description of the Figures is a graph showing the force (in Newtons—N) to be applied to move the stent in the capsule as a function of the movement (in mm). A: represents a capsule covered with stearylamine and non-crosslinked hyaluronic acid; B: represents a capsule covered with stearylamine and hyaluronic acid crosslinked with Tyzor TE 200 mM; C: represents a capsule covered with stearylamine and hyaluronic acid crosslinked with 1,4-butanediol diglycidyl ether (BDDE) 200 mM, and D: represents a capsule covered with stearylamine and hyaluronic acid crosslinked with polyethylene glycol) diglycidyl ether (PEGDGE) 200 mM.

is a graph showing the force (in Newtons—N) to be applied to move the stent in the capsule as a function of the movement (in mm). A: represents the results obtained for a capsule covered with stearylamine and hyaluronic acid crosslinked with 50 mM Tyzor TE; B; represents the results obtained for a capsule covered with stearylamine and hyaluronic acid crosslinked with 100 mM Tyzor TE;

Figure 1:
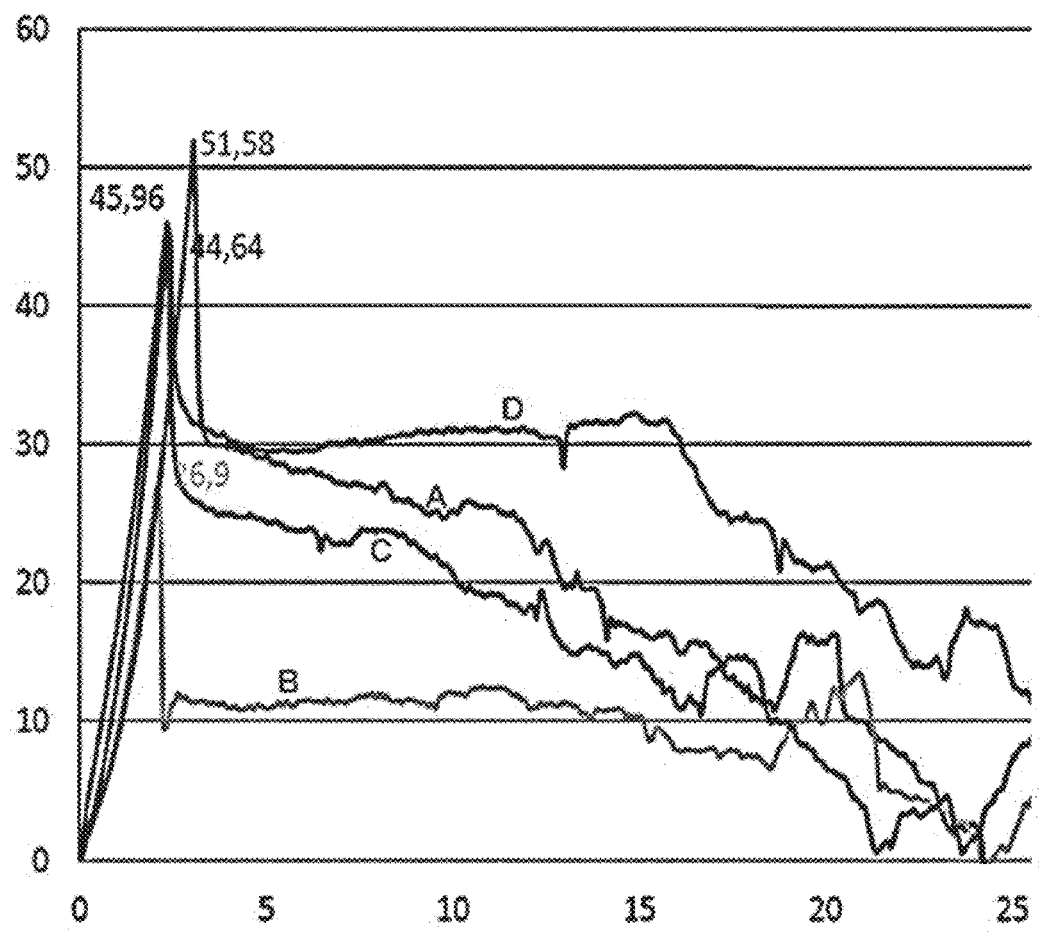

C: represents the results obtained for a capsule covered with stearylamine and hyaluronic acid crosslinked with 200 mM Tyzor TE;

D: represents the results obtained for a capsule covered with stearylamine and hyaluronic acid crosslinked with 400 mM Tyzor TE and D: represents the results obtained for a capsule covered with stearylamine and hyaluronic acid crosslinked with 800 mM Tyzor TE.

is a graph showing the forces (in N) for sliding (black bars) and resistance (white bars) on polyethylene probes that are covered with hyaluronic acid according to the method of the invention and subjected to passes through 50 g jaws over 8 cm of probe. 1: represents the results obtained for a probe covered with stearylamine and non-crosslinked hyaluronic acid; 2: represents the results obtained for a probe covered with stearylamine and hyaluronic acid crosslinked with 50 mM Tyzor TE; 3: represents the results obtained for a probe covered with stearylamine and hyaluronic acid crosslinked with 200 mM Tyzor TE; and 4; represents the results obtained for a capsule covered with stearylamine and hyaluronic acid crosslinked with 800 mM Tyzor TE. The results represent the mean and standard deviation of several tests.

EXAMPLES

Example 1

Hydrophobic Metal Surface Covering

Four metal capsules (nitinol) are washed beforehand by being vertically immersed in a beaker containing 95% ethanol. The beaker containing the capsules is subjected to ultrasound for 2 mins, then the beaker is left in a water bath at 60° C. for 1 hour. The capsules are removed from the washing solution and allowed to air dry. The capsules are then immersed vertically in a beaker containing 80 ml of 0.1% (mlv) stearylamine in dimethylformamide. The beaker containing the capsules is placed in a thermostatically controlled heating chamber at 27° C. on an orbital shaker for 1 hour. At the end of this time, the capsules are removed from the beaker and they are immersed in 3 successive baths of distilled water for washing. Finally, the capsules are immersed vertically in a beaker containing 80 ml of 0.2% (m/v) hyaluronic acid in distilled water. The beaker is stirred on an orbital shaker for 2 hours at room temperature. Finally, the capsules are removed and allowed to air dry for 24 hours.

Crosslinking

Four capsules are covered with hyaluronic acid according to the above method.

The hyaluronic acid layer is crosslinked by various crosslinking agents:

Capsule 1 (E1): non-crosslinked,

Capsule 2 (E2): crosslinked by triethanolamine titanate chelate—TYZOR TE 200 mM, Capsule 3 (E3): crosslinked by 1,4-butanediol diglycidyl ether (BDDE) 200 mM, and Capsule 4 (E4): crosslinked by polyethylene glycol) diglycidyl ether (PEGDGE) 200 mM.

The three metal capsules E2. E3, E4 are immersed vertically and in tubes containing 8 ml TYZOR TE 200 mM in distilled water, 8 ml 200 mM BDDE in 0.25N NaOH and 8 ml 200 mM PEGDGE in 0.25N NaOH, respectively, these solutions completely covering the metal capsules to be treated.

The tubes are placed on an orbital shaker for 1 hour at room temperature. At the end of this time, the capsules are removed from the solution of crosslinking agent and placed in a heating chamber at 60° C. for 60 mins for E2 and 15 mins for E3 and E4. The metal tubes are then washed with distilled water on an orbital shaker for 15 mins at room temperature. This is followed by four successive washing baths. Finally, the capsules are immersed vertically in a beaker containing 80 ml of 0.2% (m/v) hyaluronic acid in distilled water. The beaker is stirred on an orbital shaker for 2 hours at room temperature.

The crosslinking method can be repeated a second time.

The capsules are immersed in a beaker containing 80 ml of 0.3% (m/v) (hyaluronic acid in distilled water.

To evaluate the effect of the crosslinking agents, the inventors measured the stripping force. To do this, the inventors pushed a stent inside the treated capsule while measuring the force necessary to make it move forward. This is the stripping force.

The results obtained for the different instances of crosslinking are shown in FIG. 1.

The following table 1 summarizes the results in FIG. 1.

| Capsule | Stripping force (N) |
| --- | --- |
| E1 - non-crosslinked HA | 45.96 |
| E2 - HA crosslinked by TYZOR TE 200 mM | 26.90 |
| E3 - HA crosslinked by BDDE 200 mM | 44.64 |
| E4 - HA crosslinked by PEGDGE 200 mM | 51.58 |

From the data obtained, the capsule giving the best results is the E2 capsule, where only 26.9N is needed to move a stent.

The E1 and E3 capsules gave slightly lower results than an untreated capsule (no covering; not shown): an average of 45.3N for these two capsules compared with 53.7N for an untreated capsule.

The E4 capsule gives results equivalent to an untreated capsule (51.6N compared with 53.7N).

The crosslinking agents are therefore not equivalent, and TYZOR TE is the best crosslinking agent and allows good surface lubrication.

Example 2

In this example, capsules are covered as indicated in example 1, in the section "Hydrophobic surface covering."

Crosslinking

Five capsules are covered with hyaluronic acid according to the above method.

The hyaluronic acid layer is crosslinked by TYZOR TE at different concentrations:

Capsule 1 (E1a): by TYZOR TE 50 mM,

Capsule 2 (E2a): by TYZOR TE 100 mM,

Capsule 3 (E3a): by TYZOR TE 200 mM,
Capsule 4 (E4a): by TYZOR TE 400 mM, and
Capsule 5 (E5a): by TYZOR TE 800 mM.

The five metal capsules E1a, E2a, E3a, E4a and E5a are immersed vertically in tubes containing 8 ml TYZOR TE 50, 100, 200, 400 and 800 mM, respectively, in distilled water, these solutions completely covering the metal capsules to be treated. The tubes are placed on an orbital shaker for 1 hour at room temperature.

At the end of this time, the capsules are removed from the solution of crosslinking agent and placed in a heating chamber at 60° C. for 60 mins. The metal tubes are then washed with distilled water on an orbital shaker for 15 mins at room temperature. This is followed by four successive washing baths. Finally, the capsules are immersed vertically in a beaker containing 80 ml of 0.2% (m/s') hyaluronic acid in distilled water. The beaker is stirred on an orbital shaker for 2 hours at room temperature.

The crosslinking method can be repeated a second time. In this case, the capsules are immersed in a beaker containing 80 ml of 0.3% (m/v) hyaluronic acid in distilled water.

Results

To evaluate the effect of the crosslinking agents, the inventors measured the stripping force. To do this, the inventors pushed a stent inside the treated capsule while measuring the force necessary to make it move forward. This is the stripping force.

Figure 2:
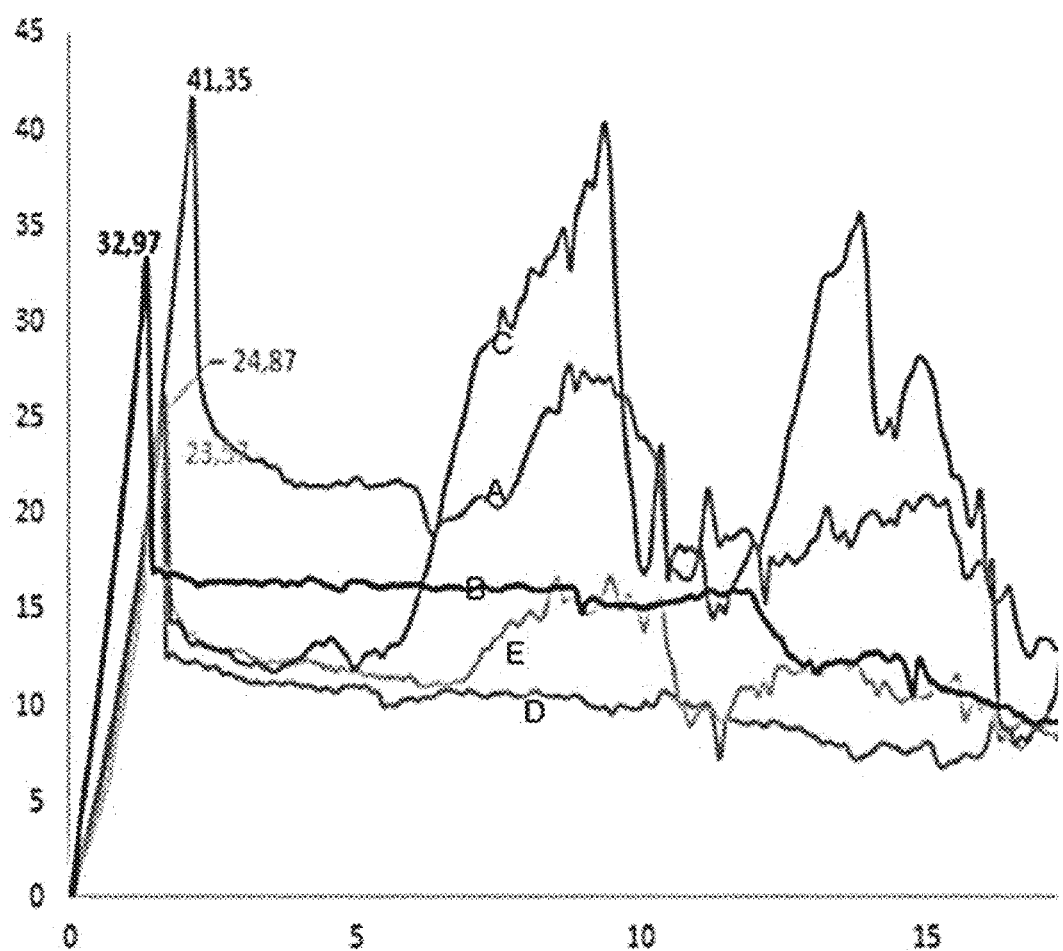

The results obtained for the different instances of crosslinking are shown in FIG. 2.

The following table 2 summarizes the results in said figure.

| Capsule | Stripping force (N) |
| --- | --- |
| E1a - HA crosslinked by TYZOR TE 50 mM | 41.3 |
| E2a - HA crosslinked by TYZOR TE 100 mM | 33.0 |
| E3a - HA crosslinked by TYZOR TE 200 mM | 26.0 |
| E4a - HA crosslinked by TYZOR TE 400 mM | 24.5 |
| E5a - HA crosslinked by TYZOR TE 800 mM | 23.6 |

The efficiency of the sliding is dose-dependent on the concentration of the crosslinking agent (TYZOR TE). The more crosslinking agent is present, the more the sliding makes it possible to retain the layer of non-crosslinked hyaluronic acid.

Example 3

Hydrophobic Polymer Surface Covering

Polyethylene probes are washed beforehand by being vertically immersed in a beaker containing 95% ethanol. The beaker containing the probes is subjected to ultrasound for 2 min, then the beaker is left in a water bath at 60° C. for 1 hour. The probes are removed from the washing solution and allowed to air dry. The probes are then immersed vertically in a beaker containing a solution of 0.1% (m/v) stearylamine in dimethylformamide. The beaker containing the probes is placed in a thermostatically controlled heating chamber at 27° C. on an orbital shaker for 1 hour. At the end of this time, the probes are removed from the beaker and they are immersed in 3 successive baths of distilled water for washing. Finally, the probes are immersed vertically in a beaker containing a solution of 0.2% (m/v) hyaluronic acid in distilled water. The beaker is stirred on an orbital shaker for 2 hours at room temperature.

Finally, the probes are removed and allowed to air dry for 24 hours.

The probes are covered with hyaluronic acid according to the method described above. The probes are divided into 4 batches.

The hyaluronic acid layer is crosslinked by TYZOR TE at different concentrations:
Batch 1: non-crosslinked,
Batch 2: crosslinked by TYZOR TE 50 mM,
Batch 3: crosslinked by TYZOR TE 200 mM, and
Batch 4: crosslinked by TYZOR TE 800 mM.

The probes of batches 2, 3 and 4 are immersed vertically in tubes containing a solution of TYZOR TE 50 mM, 200 mM, and 800 mM, respectively, in distilled water; these solutions completely cover the polyethylene probes to be treated.

The tubes are placed on an orbital shaker for 1 hour at room temperature. At the end of this time, the probes are removed from the solution of crosslinking agent and placed in a heating chamber at 60° C. for 60 mins. The probes are then washed with distilled water on an orbital shaker for 15 mins at room temperature. This is followed by four successive washing baths. Finally, the probes are immersed vertically in a beaker containing a solution of 0.2% (mlv) hyaluronic acid in distilled water. The beaker is stirred on an orbital shaker for 2 hours at room temperature.

The crosslinking method is repeated a second time.

Finally, the probes of batch 1 (non-crosslinked), and batch 2, 3 and 4 (crosslinked) are immersed in a beaker containing a solution of 0.3% (m/v) hyaluronic acid in distilled water.

To evaluate the effect of the crosslinking agents, the inventors carried out sliding and/or resistance tests with a pass through 50 g jaws over 8 cm of probes hydrated by immersion in distilled water just before the measurement.

The sliding coefficients of friction (sliding CoF) are estimated by a mean of the coefficients of the first pass through the jaws.

The resistance coefficients of friction (resistance CoF) correspond to the mean of 5 passes of the same probe.

Figure 3:
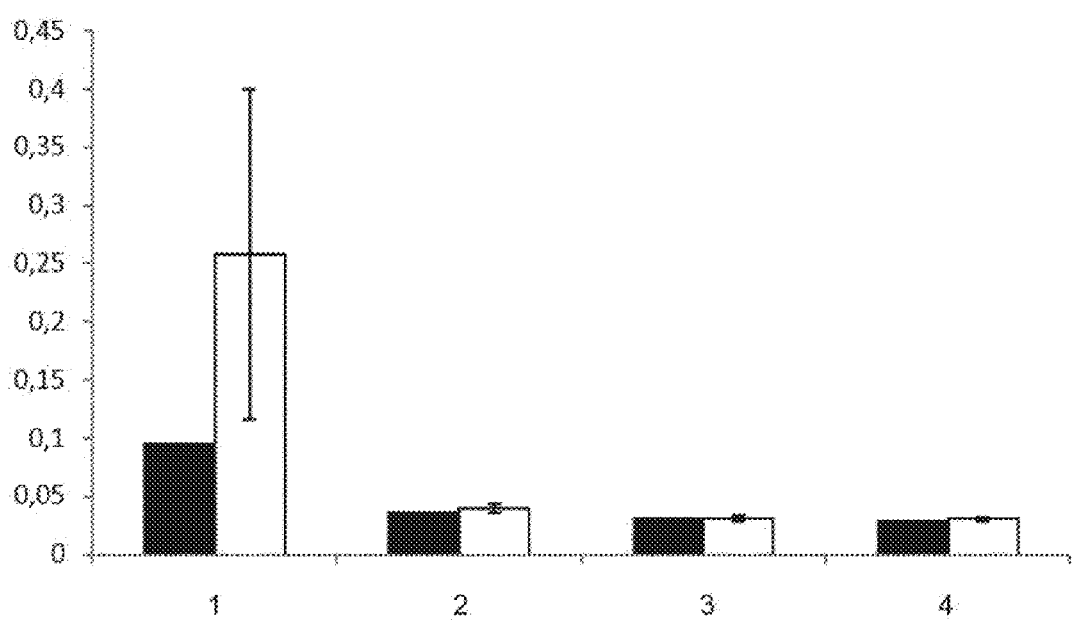

The results are shown in FIG. 3, and in the following table:

| | Sliding CoF | Standard deviation | Resistance CoF | Standard deviation |
| --- | --- | --- | --- | --- |
| Batch 1 | 0.0946 | II | 0.2577 | 0.1418 |
| Batch 2 | 0.0363 | II | 0.0401 | 0.0037 |
| Batch 3 | 0.0307 | II | 0.0309 | 0.0021 |
| Batch 4 | 0.0281 | II | 0.0304 | 0.0017 |

The results show that the crosslinking of the layer of hyaluronic acid significantly improves the sliding and very significantly improves the resistance of the covering even after several friction passes, compared with the control probe.

The invention is not limited to the embodiments presented here and other embodiments will become clearly apparent to a person skilled in the art.

The invention claimed is:

1. A method for lubricating an element essentially consisting of hyaluronic acid crosslinked by means of a crosslinking agent which is a titanium chelate or zirconium chelate that is soluble in water, the method comprising:
    a). bringing the element into contact with a solution of free hyaluronic acid, in order to obtain an element covered by free hyaluronic acid, which is a lubricated element; and wherein the crosslinking agent is a chelate of formula 1 below:

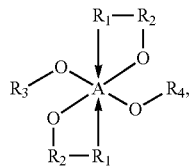

(1)

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

2. The method according to claim 1, further comprising the steps of
   b) crosslinking the free hyaluronic of the lubricated element by using a crosslinking agent of formula 1 in order to obtain a second layer of composition essentially consisting of crosslinked hyaluronic acid, and
   c) bringing the second layer of composition essentially consisting of crosslinked hyaluronic acid into contact with a solution of free hyaluronic acid, in order to obtain an element covered by a second layer of composition which is lubricated.

3. The method according to claim 2, wherein steps b) and c) are repeated at least once.

4. A lubricated element essentially consisting of at least one layer of hyaluronic acid crosslinked by a crosslinking agent which is a titanium chelate that is soluble and stable in water, the at least one layer of crosslinked hyaluronic acid being covered by a layer of non-crosslinked hyaluronic acid; and
   wherein the crosslinking agent is a chelate of formula 1 below:

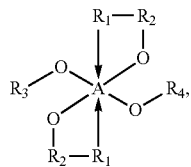

(1)

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

5. A method for lubricating a hydrophobic support comprising the steps of:
   a. covering the hydrophobic support with a first composition comprising
      a solvent, and
      a solute selected from stearylamine or stearic acid, to obtain a support covered with the first composition, the solvent being compatible with the solute and the hydrophobic surface;
   b. rinsing the hydrophobic support covered with the first composition with an aqueous solution in order to obtain a hydrophobic support covered with the first rinsed composition;
   c. bringing the hydrophobic support covered with the first rinsed composition into contact with free hyaluronic acid in order to obtain a surface having free hyaluronic acid;
   d. crosslinking the free hyaluronic acid present on the surface obtained in the previous step by using a crosslinking agent in order to obtain a first layer of crosslinked hyaluronic acid; and
   e. bringing the first layer of crosslinked hyaluronic acid into contact with a solution of free hyaluronic acid in order to obtain a lubricated hydrophobic support,
   wherein the crosslinking agent is a water-soluble titanium chelate or zirconium chelate; and
   wherein the crosslinking agent is a chelate of formula 1 below:

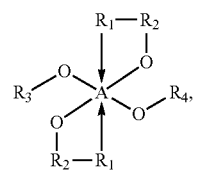

(1)

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

6. The method according to claim 5, wherein steps d) and e) are repeated at least once.

7. A lubricated hydrophobic support covered with a first layer of stearylamine or stearic acid, the first layer of stearylamine or stearic acid being covered by a first layer of hyaluronic acid crosslinked by a crosslinking agent which is a water-soluble titanium chelate or zirconium chelate; and
   wherein the crosslinking agent is a chelate of formula 1 below:

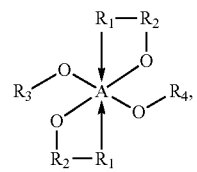

(1)

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

8. The Lubricated hydrophobic support according to claim 7, wherein

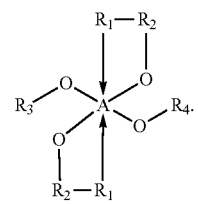

the first layer of crosslinked hyaluronic acid is covered by a second layer of free hyaluronic acid.

9. A kit including:
a. a first composition essentially consisting of stearylamine or stearic acid;
b. a second composition comprising or essentially consisting of hyaluronic acid; and
c. a crosslinking compound, the crosslinking compound being a water-soluble titanium chelate or zirconium chelate; and
  wherein the crosslinking agent is a chelate of formula 1 below:

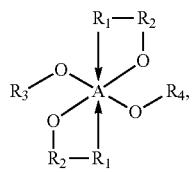

(1)

where A is Ti, and
where $R_1$ is a functional group containing an oxygen or nitrogen atom, $R_2$ represents two or three carbon atoms, and $R_3$ and $R_4$ represent a linear or branched or cyclic $C_1$-$C_4$ alkyl.

10. A method for lubricating an element essentially consisting of hyaluronic acid crosslinked by means of a crosslinking agent which is a titanium chelate or zirconium chelate that is soluble in water, the method comprising:
a). bringing the element into contact with a solution of free hyaluronic acid, in order to obtain an element covered by free hyaluronic acid, which is a lubricated element; and
wherein the crosslinking agent is selected from a group consisting of:

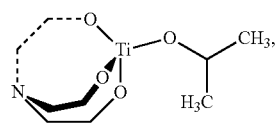

(1a1)

and Dihydroxybis(ammonium lactato)titanium(IV) (1a2).

* * * * *